US010124160B2

United States Patent
Dorvall, II et al.

(10) Patent No.: US 10,124,160 B2
(45) Date of Patent: Nov. 13, 2018

(54) CHARGE STEERING HIGH DENSITY ELECTRODE ARRAY

(71) Applicant: University of Utah Research Foundation, Salt Lake City, UT (US)

(72) Inventors: Alan Dale Dorvall, II, Salt Lake City, UT (US); Andrew Colin Willsie, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/401,213

(22) PCT Filed: May 16, 2013

(86) PCT No.: PCT/US2013/041292
§ 371 (c)(1),
(2) Date: Nov. 14, 2014

(87) PCT Pub. No.: WO2013/173551
PCT Pub. Date: Nov. 21, 2013

(65) Prior Publication Data
US 2015/0148869 A1 May 28, 2015

Related U.S. Application Data

(60) Provisional application No. 61/647,780, filed on May 16, 2012.

(51) Int. Cl.
*A61N 1/05* (2006.01)
*A61N 1/36* (2006.01)

(52) U.S. Cl.
CPC ....... *A61N 1/0534* (2013.01); *A61N 1/36139* (2013.01); *A61N 1/36182* (2013.01); *A61N 1/36185* (2013.01); *A61N 1/3615* (2013.01)

(58) Field of Classification Search
CPC ................ A61N 1/0534; A61N 1/3615; A61N 1/36139; A61N 1/36182; A61N 1/36185
See application file for complete search history.

(56) References Cited

U.S. PATENT DOCUMENTS 5,215,088 A 6/1993 Normann et al.
7,447,551 B2 11/2008 Kuo et al.
(Continued)

FOREIGN PATENT DOCUMENTS

EP 1723983 A1 11/2006
WO WO 2008/109298 A2 9/2008
(Continued)

OTHER PUBLICATIONS

Binder et al.; "Hemorrhagic complications of microelectrode-guided deep brain stimulation;" Stereotact Funct Neurosurg 80, 28-31 (2003).
(Continued)

*Primary Examiner* — Joseph Dietrich
(74) *Attorney, Agent, or Firm* — Thorpe North & Western, LLP

(57) ABSTRACT

Technology for deep brain stimulating including devices, systems, computer circuitry, and associated methods is provided. A deep brain stimulating device (100) can include a semiconductor substrate, an array of electrodes (140) coupled to the semiconductor substrate, and circuitry operable to control the array of electrodes (140). Each electrode (142) can be operable to function as an anode, a cathode, a common, or a float independent of other electrodes in the array to create highly configurable electric fields (122, 124).

27 Claims, 10 Drawing Sheets

(56) References Cited

U.S. PATENT DOCUMENTS

| | | |
|---|---|---|
| 7,769,472 B2 | 8/2010 | Gerber |
| 7,797,029 B2 | 9/2010 | Gibson et al. |
| 8,209,023 B2 | 6/2012 | Zhou et al. |
| 8,332,046 B2 | 12/2012 | Anderson et al. |
| 8,352,045 B2 | 1/2013 | Joucla et al. |
| 8,359,083 B2 | 1/2013 | Clark et al. |
| 8,423,143 B2 | 4/2013 | Bartic et al. |
| 2006/0253182 A1 | 11/2006 | King |
| 2006/0265039 A1* | 11/2006 | Bartic .................. A61N 1/0531 607/116 |
| 2006/0276866 A1 | 12/2006 | McCreery |
| 2007/0055322 A1 | 3/2007 | Forsberg et al. |
| 2007/0197892 A1 | 8/2007 | Shen et al. |
| 2008/0188909 A1 | 8/2008 | Bradley |
| 2008/0215125 A1* | 9/2008 | Farah .................. A61N 1/36082 607/116 |
| 2009/0018617 A1* | 1/2009 | Skelton .................. A61N 1/056 607/59 |
| 2009/0240314 A1 | 9/2009 | Kong et al. |
| 2010/0030298 A1 | 2/2010 | Martens et al. |
| 2010/0063450 A1 | 3/2010 | Smith et al. |
| 2010/0076535 A1 | 3/2010 | Pianca et al. |
| 2011/0130817 A1 | 6/2011 | Chen |
| 2011/0172737 A1 | 7/2011 | Davis et al. |
| 2011/0313236 A1 | 12/2011 | Valente et al. |
| 2012/0109262 A1 | 5/2012 | Martens |
| 2012/0150256 A1 | 6/2012 | Martens |
| 2012/0296271 A1 | 11/2012 | Yomtov et al. |
| 2013/0090525 A1 | 4/2013 | Seymour et al. |

FOREIGN PATENT DOCUMENTS

| | | | |
|---|---|---|---|
| WO | WO 2009/009724 A1 | 1/2009 | |
| WO | WO 2009/052425 A1 | 4/2009 | |
| WO | WO 2010/055421 A1 | 5/2010 | |
| WO | WO 2010/058178 A1 | 5/2010 | |
| WO | WO 2011/067297 A1 | 6/2011 | |

OTHER PUBLICATIONS

Bour et al.; "Long-term experience with intraoperative microrecording during DBS neurosurgery in STN and GPi;" Acta Neurochir (Wien) 152, 2069-2077 (2010).

Burdick et al.; "Do patient's get angrier following STN, GPi, and thalamic deep brain stimulation;" Neuroimage 54 Suppl 1, S227-232 (2011).

Butson et al.; "Probabilistic analysis of activation volumes generated during deep brain stimulation." Neuroimage 54, 2096-2104 (2011).

Butson et al.; "Current steering to control the volume of tissue activated during deep brain stimulation." Brain Stimul 1, 7-15 (2008).

Chaturvedi et al.; "Current steering to activate targeted neural pathways during deep brain stimulation of the subthalamic region;" Brain stimulation (2011).

Kang et al.; "Cerebral ischemia related to globus pallidus internus stimulation for cervical dystonia". Stereotact Funct Neurosurg 89, 201-204 (2011).

Kazemi et al.; "A test microchip for evaluation of hermetic packaging technology for biomedical prosthetic implants;" Conf Proc IEEE Eng Med Biol Soc 6, 4093-4095 (2004).

Koop et al.; "Improvement in a quantitative measure of bradykinesia after microelectrode recording in patients with Parkinson's disease during deep brain stimulation surgery". Movement Disorders 21, 673-678 (2006).

Martens et al. "Spatial steering of deep brain stimulation volumes using a novel lead design;" Clin Neurophysiol 122, 558-566 (2011).

McClelland, S., $3^{rd}$; "A cost analysis of intraoperative microelectrode recording during subthalamic stimulation for Parkinson's disease;" Mov. Disord. 26, 1422-1427 (2011).

McIntyre et al.; "Improving postural stability via computational modeling approach to deep brain stimulation programming;" Conf Proc IEEE Eng Med Biol Soc 2011, 675-676 (2011).

McIntyre et al.; Customizing deep brain stimulation to the patient using computational models; Conf Proc IEEE Eng Med Biol Soc 2009, 4228-4229 (2009).

Neves et al.; "The NeuroProbes project: A concept for electronic depth control;" Engineering in Medicine and Biology Society, 2008. EMBS 2008. 30th Annual International Conference of the IEEE 1857 (2008).

Seidl et al, "CMOS-Based High-Density Silicon Microprobe Array for Electronic Depth Control in Neural Recording", IEEE, 2009, 232-235.

Vasques et al.; "A target-specific electrode and lead design for internal globus pallidus deep brain stimulation." Stereotact Funct Neurosurg 88, 129-137 (2010).

Xiaowu et al.; "Risks of intracranial hemorrhage in patients with Parkinson's disease receiving deep brain stimulation and ablation". Parkinsonism Relat. Disord. 16, 96-100 (2010).

Anderson et al., "Wireless Implantable Microsystems: High-Density Electronic Interfaces to the Nervous System", Proceedings of the IEEE, Jan. 1, 2004, pp. 76-97, vol. 92 No. 1, New York, US.

* cited by examiner

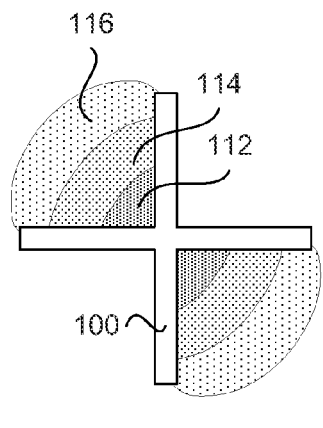
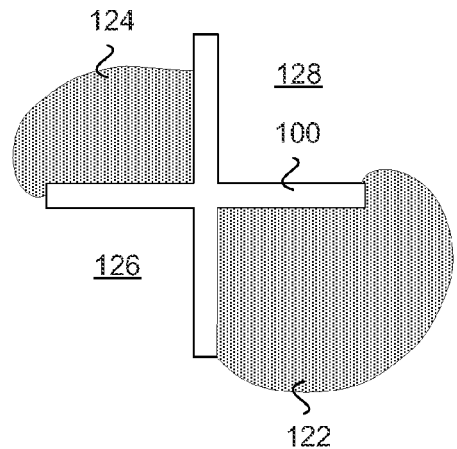
FIG. 1            FIG. 2A
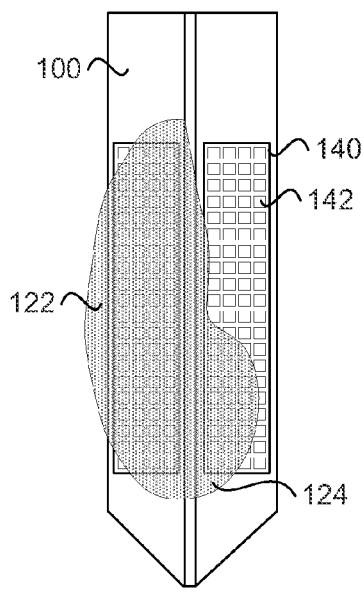
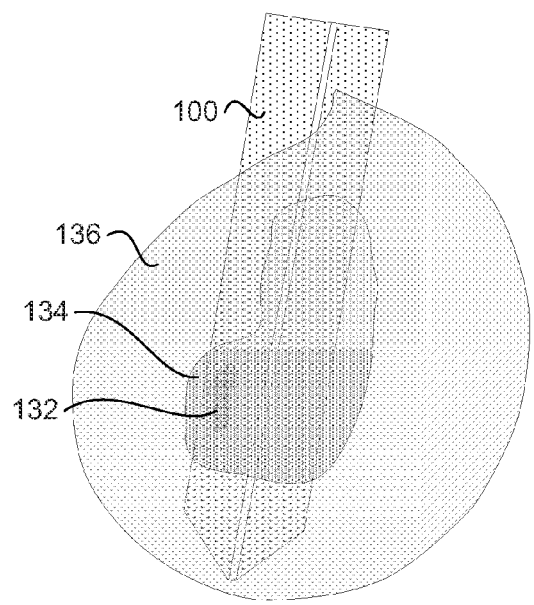
FIG. 2B           FIG. 2C

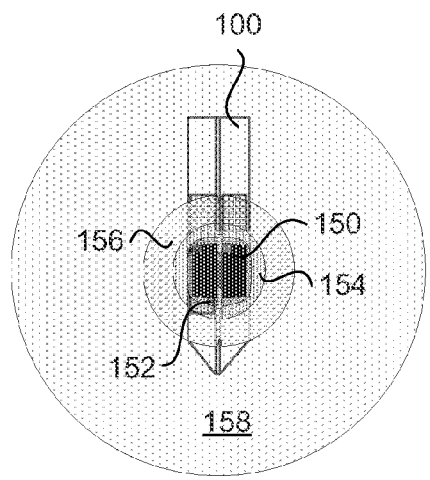 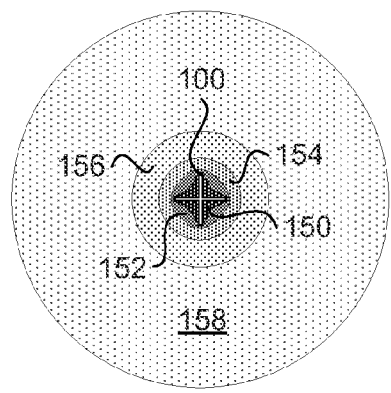
FIG. 3A              FIG. 3B
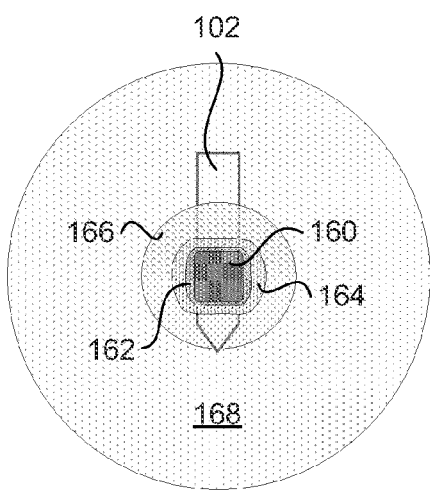 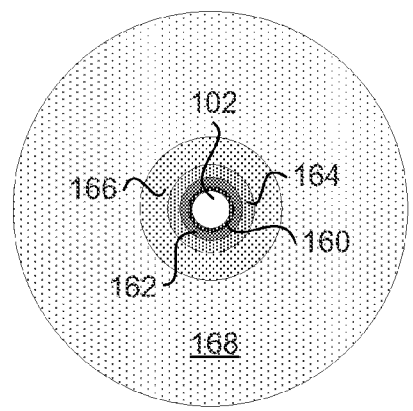
FIG. 4A              FIG. 4B

CHARGE STEERING HIGH DENSITY ELECTRODE ARRAY

RELATED APPLICATIONS

This application claims the benefit of and hereby incorporates by reference U.S. Provisional Patent Application Ser. No. 61/647,780, filed May 16, 2012.

GOVERNMENT INTEREST

This invention was made with government support under K25 NS053544 awarded by the National Institutes of Health. The government has certain rights in the invention.

FIELD OF THE INVENTION

The present invention relates generally to technology for deep brain stimulation (DBS). Accordingly, the present invention involves using an array of electrodes which can be implanted in the brain to provide controllable electrical fields for DBS.

BACKGROUND OF THE INVENTION

Deep brain stimulation (DBS) is a surgical treatment involving the implantation of a medical device that sends electrical current pulses to specific regions of the brain. DBS in select brain regions has provided various therapeutic benefits for otherwise treatment-resistant movement and affective disorders such as chronic pain, Parkinson's disease, tremor, dystonia, and the like. DBS directly changes brain activity in a controlled manner. DBS effects can be reversible, unlike changes affected by lesioning techniques.

Most DBS systems include three component parts: an implanted pulse generator (IPG), a lead, and an extension. The IPG can use a battery-powered neurostimulator encased in a titanium housing that sends electrical current pulses to the brain in order to interfere with or otherwise modify neural activity at a target site. The lead can be a coiled insulated wire with four platinum iridium electrodes placed in the brain. The lead can be connected to the IPG by the extension, an insulated wire that runs from the head, down the side of the neck, behind the ear to the IPG. The IPG can be placed subcutaneously below the clavicle or in some cases, the abdomen.

While DBS can be helpful for some patients, DBS also has the potential for serious side effects. Reports in the literature describe the possibility of apathy, hallucinations, compulsive gambling, hypersexuality, cognitive dysfunction, and depression. Such side effects may be related to the incorrect placement and calibration of the stimulator. Because the brain can shift slightly during surgery, there is the possibility that the electrodes can become displaced or dislodged. The misplacement of the lead (e.g., electrode) may cause more profound complications such as personality changes, potentially requiring electrode repositioning.

SUMMARY OF THE INVENTION

Deep brain stimulating devices, systems, and associated methods are provided. In one aspect, a deep brain stimulating device can include a semiconductor substrate, an array of electrodes coupled to the semiconductor substrate, and circuitry operable to control the array of electrodes. Each electrode can be operable to function as an anode, a cathode, a common, or a float independent of other electrodes in the array. The common can be a specified voltage between the anode and cathode. The semiconductor substrate can include at least two surfaces and each surface can include at least two columns of electrodes and at least two rows of electrodes. In one specific aspect, the array of electrodes includes from about 50 to about 25,000 electrodes. In another aspect, the array of electrodes includes from about 5000 to about 15,000 electrodes. In yet another aspect, the array of electrodes includes greater than 25,000 electrodes.

Various structural configurations are contemplated to support the array of electrodes. In one aspect, for example, the semiconductor substrate includes at least two surfaces that are perpendicular to one another, where each of the two surfaces includes a portion of the array of electrodes. In another aspect, the semiconductor substrate is formed into a plus shape having eight perpendicularly opposed surfaces, wherein each of the eight perpendicularly opposed surfaces includes a portion of the array of electrodes. The semiconductor substrate can include the circuitry operable to control the array of electrodes. The circuitry can also include a shift register.

In another aspect, a deep brain stimulating system is provided. Such a system can include a deep brain stimulating device including a semiconductor substrate an array of electrodes coupled to the semiconductor substrate, and circuitry operable to control the array of electrodes. Each electrode can be operable to function as an anode, a cathode, a common, or a float independent of other electrodes in the array. The system can also include an implanted pulse generator and an electrical connection extension electrically coupling the circuitry of the deep brain stimulating device to the implanted pulse generator.

In yet another aspect, a method of stimulating a neural region in vivo is provided. Such a method can include identifying a region of neural tissue to be electrically stimulated, where the region of neural tissue has an irregular three dimensional surface area, inserting a stimulating electrode into a location in proximity to the region of neural tissue, and delivering an electric field from the stimulating electrode that substantially matches the three dimensional boundaries of the region of neural tissue. In one specific aspect, the location in proximity to the region of neural tissue is in a portion of the three dimensional volume. In another aspect, the electric field is delivered in an asymmetrical pattern relative to a longitudinal axis of the stimulating electrode. In yet another aspect, the electric field is delivered in an asymmetrical pattern relative to a lateral axis of the stimulating electrode. The stimulating electrode can include an array of electrodes with at least two columns of electrodes and at least two rows of electrodes.

In a configuration, the operation of delivering an electric field from the stimulating electrode that substantially matches the three dimensional volume of the region of neural tissue can further include: delivering an electric field from the stimulating electrode that estimates the three dimensional boundaries of the region of neural tissue; measuring the electric field from the stimulating electrode relative to the region of neural tissue; and adjusting the electric field of the stimulating electrode to substantially spatially match the three dimensional boundaries of the region of neural tissue. In another configuration, the operation of delivering an electric field from the stimulating electrode that substantially matches the three dimensional boundaries of the region of neural tissue can further include: delivering an electric field from the stimulating electrode that estimates the three dimensional volume of the region of neural tissue; evaluating the effect of the electric field from the stimulating electrode; and adjusting the electric field of the stimulating electrode based on the effect to minimize an adverse side effect of the electric field.

In another aspect, an array of electrodes for deep brain stimulation (DBS) can include computer circuitry. The computer circuitry can be configured to generate an electric field to stimulate a specified region of neural tissue using the array of electrodes, and adjust the electric field using a configurable pattern of pulses generated by the array of electrodes. Each electrode can be operable to function as an anode, a cathode, a common, or a float independent of other electrodes in the array. The computer circuitry can include at least two columns of electrodes and at least two rows of electrodes. The computer circuitry can include a shift register to control the array of electrodes. The electric field is generated in an asymmetrical pattern relative to a longitudinal axis or lateral axis of the array of electrodes.

There has thus been outlined, rather broadly, the more important features of the disclosure so that the detailed description that follows may be better understood, and so that the present contribution to the art may be better appreciated. Other features of the disclosure will become clearer from the following detailed description of the disclosure, taken with the accompanying drawings and claims, or may be learned by the practice of the disclosure.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure.

FIG. 1 illustrates a cross-sectional view graphical representation of the generation of an electric field using a deep brain stimulating device in accordance with an example;

FIG. 2A illustrates a cross-sectional view graphical representation of simulation data showing two simultaneous asymmetrical electric fields using a deep brain stimulating device in accordance with an example;

FIG. 2B illustrates a side view graphical representation of simulation data showing two simultaneous asymmetrical electric fields using a deep brain stimulating device in accordance with an example;

FIG. 2C illustrates a side view graphical representation of simulation data showing isopotential surfaces (e.g., electric fields) using a deep brain stimulating device in accordance with an example;

FIG. 3A illustrates a side view graphical representation of simulation data showing isopotential surfaces (e.g., electric fields) using a deep brain stimulating device including an array of electrodes in accordance with an example;

FIG. 3B illustrates an axial view graphical representation of simulation data showing isopotential surfaces (e.g., electric fields) using a deep brain stimulating device including an array of electrodes in accordance with an example;

FIG. 4A illustrates a side view graphical representation of simulation data showing isopotential surfaces (e.g., electric fields) using a deep brain stimulating device in accordance with an example;

FIG. 4B illustrates an axial view graphical representation of simulation data showing isopotential surfaces (e.g., electric fields) using a deep brain stimulating device in accordance with an example;

Figure 5A:
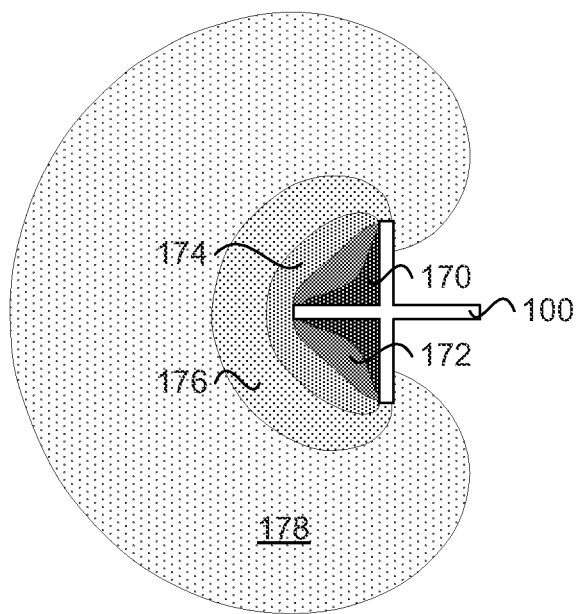
FIG. 5A illustrates a side view graphical representation of simulation data showing isopotential surfaces (e.g., electric fields) using a deep brain stimulating device in accordance with an example.

These drawings merely depict exemplary embodiments of the disclosure, therefore, the drawings are not to be considered limiting of its scope. It will be readily appreciated that the components of the disclosure, as generally described and illustrated in the figures herein, could be arranged, sized, and designed in a wide variety of different configurations. Nonetheless, the disclosure will be described and explained with additional specificity and detail through the use of the accompanying drawings.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting. The same reference numerals in different drawings represent the same element.

It must be noted that, as used in this specification and the appended claims, the singular forms "a," "an," and "the" include plural referents unless the context clearly dictates otherwise. Thus, for example, reference to "an electrode" includes one or more of such electrodes, reference to "the conductor" includes reference to one or more of such conductors, and reference to "stimulating" includes one or more of such steps.

In describing and claiming the present invention, the following terminology will be used in accordance with the definitions set forth below.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or subranges encompassed within that range as if each numerical value and sub-range is explicitly recited. As an illustration, a numerical range of "about 0.6 mm to about 0.3 mm" should be interpreted to include not only the explicitly recited values of about 0.6 mm and about 0.3 mm, but also include individual values and sub-ranges within the indicated range. Thus, included in this numerical range are individual values such as 0.4 mm and 0.5, and sub-ranges such as from 0.5-0.4 mm, from 0.4-0.35, etc. This same principle applies to ranges reciting only one numerical value. Furthermore, such an interpretation should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill in the art. Further, unless otherwise stated, the term "about" shall expressly include "exactly," consistent with the discussion above regarding ranges and numerical data.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the disclosure should be determined solely by the appended claims and their legal equivalents, rather than by the descriptions and examples given herein.

Neural stimulation electrodes, electrode arrays, and methods of making and using such devices are provided. In one aspect, for example, such an electrode can be a deep brain stimulating (DBS) device that includes an electrode array capable of generating a wide variety of electric field patterns. The patterns of electric fields can range from relatively uniform spherical patterns (FIGS. 3A-3B) to complex asymmetrical patterns (FIGS. 2A-C), which are described in more detail below. To achieve such configurability, the device can include an array of configurable anodes and cathodes spatially arranged such that selective activation of various anodes and cathodes create different patterns of electric fields. The device can include any number of anode and cathode electrodes, and these electrodes can be arranged into any useful configuration. The number and arrangements of electrodes can also affect the complexity of the electric field patterns that can be generated. For example, in one aspect, a DBS device can have up to 10,000 electrodes or more. If each of these electrodes is assumed to have 4 states (anode, cathode, common, floating), the device would be capable of $4^{10,000}$ or $\sim 4 \times 10^{6020}$ combinations of electrode settings. Such flexibility can facilitate precise control over how electrical charge is delivered to the brain tissue, allowing electrical charge steering and unique activation geometries not previously achievable with traditional DBS devices.

FIG. 1 shows one example of a DBS device 100 having a plus-shape (+). FIG. 1 shows a cross section through the plus-shaped device, with a gradient showing the strength of the electric field in one particularly unique configuration. The near electric field 112 to the DBS device can have a greater intensity (e.g., larger gradient) than the middle electric field 114, and the far electric field 116 electric field can have less intensity (e.g., smaller gradient) than the middle electric field. Thus, the electric field can be adjusted to spatially match a region of tissue and to also adjust the intensity of the electric field throughout the electric field. FIGS. 2A-2C illustrate an asymmetrical surface of one iso-potential shell of two simultaneous asymmetrical electric fields 122 and 124 from different angles. FIG. 2A illustrates a cross-sectional view or axial view of the iso-potential shell (e.g. an electric field at a specified voltage). FIG. 2A illustrates a cross-sectional view or axial view of the iso-potential shell. FIG. 2B illustrates a side view or view along the longitudinal axis of the iso-potential shell. FIG. 2B also depicts individual electrode contacts 142 of the electrode array 140 on the DBS surface.

As shown in FIG. 2A, electrodes in two sections (e.g., quarters) of the DBS device can be activated to generate electric fields 122 and 124, while two sections 126 and 128 can be inactivated and thus do not generate electric fields 16. Similar spatial activation lengthwise along the DBS device can generate a similar configurability of electrical fields 122 and 124 along the longitudinal axis of the device, as shown in FIG. 2B. FIG. 2C illustrates yet another potential configuration for configurable electric fields with three different iso-potential shells 132, 134 and 136, having decreasing strength respectively. As such, stimulating current can be steered (see FIG. 11) to a targeted brain region, providing at least substantially complete coverage of the neural target and thus better symptom alleviation, and eliminating or reducing excess stimulation outside the target region, thereby removing side effects. Thus, the device has a configurable electric field radially and longitudinally across the device. It is noted that the shape and overall configuration of a DBS device may not be limited to a plus shape, and that the device is contemplated to have any shape capable of allowing configuration of the electric field according to aspects of the present disclosure are considered to be within the present scope. Non-limiting examples can include asterisks (*), 'L' shapes (including obtuse, acute and 90° angles), planar shapes, semicircular shapes, circular shapes, gammadion shapes, asymmetric shapes, and the like. The shape of the device can typically be configured to facilitate insertion of the device into tissue while minimizing tissue damage. As such, in some embodiments, the cross-sectional shape can include flatted features such that the smallest dimension is substantially less than the longest dimension (i.e. a high ratio of thickness to width).

The DBS device can be fabricated from a variety of materials, and any such material is considered to be within the present scope. Materials can be chosen based on mechanical strength, device performance, and ease of manufacturing. For example, many semiconductor materials (e.g., silicon) have sufficient mechanical strength while also providing a suitable substrate into which the configurable electrode array can be formed. Although other materials may be used, the DBS device can be fabricated from a semiconductor material, insulating material (e.g., ceramic, glass or other insulators), polymers, or the like. Any useful semiconductor material can be used; however, one example includes silicon.

Figure 7:
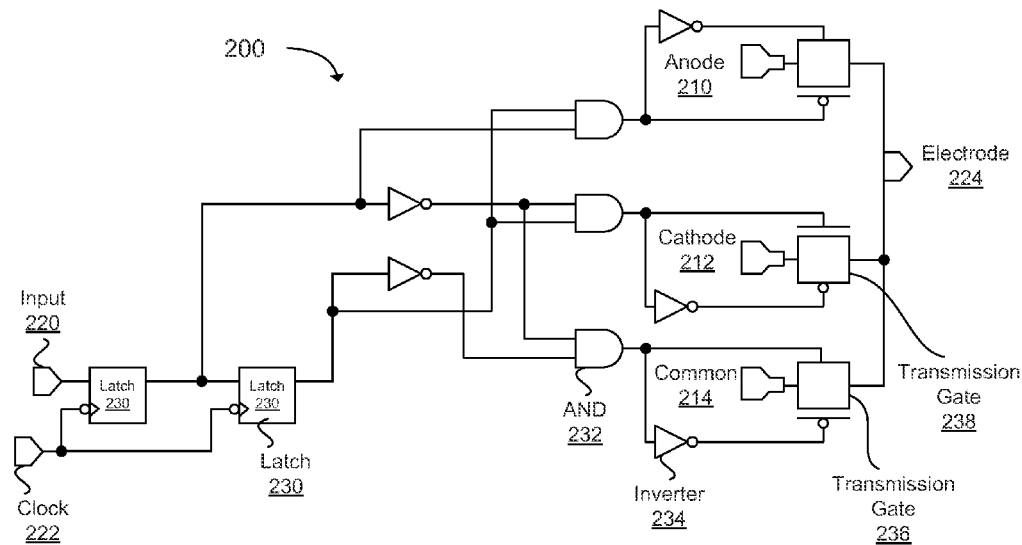
FIG. 7 illustrates a circuit diagram of circuitry used a deep brain stimulating device in accordance with an example.
Figure 8:
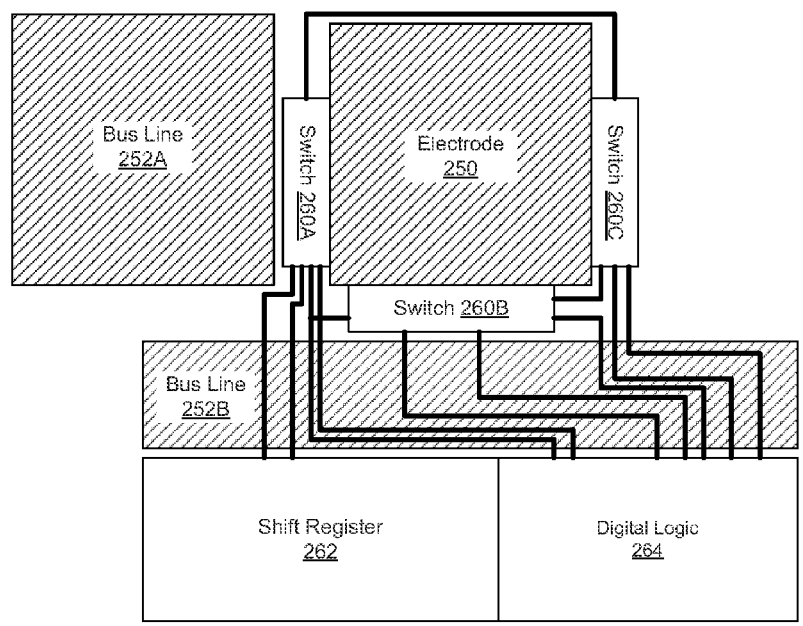
FIG. 8 illustrates a generalized semi-conductor layout (e.g., transistor level view) of circuitry used a deep brain stimulating device in accordance with an example.

In another example, the DBS device can include onboard circuitry to connect bus lines to the electrode contacts (see FIGS. 7-8). Any number of bus lines is contemplated, however in one aspect the DBS device can include three bus lines: An anode bus line, a cathode bus line, and a common bus line. The circuitry can be formed on a common semiconductor substrate with the electrodes, however a separate substrate may be used. For example, the circuitry can be fabricated in the manner, although "flip chip" bonding can be used to bond a secondary substrate, connecting the thousands of contacts in a single step. The secondary substrate could be made out of any suitable material, and processing of bond pads can be done to match the "flip chip" sites on the circuit.

In one specific aspect, silicon members can be arranged into a plus ("+") shape such that electrode contacts in the silicon members are facing each of four directions with each substrate face being isolated from the 180 degree opposite face as shown in FIG. 1. In other words, an electrical field activated in one direction can be inhibited from flowing in the opposite direction. Further, the plus shape configuration allows for four segmented regions each of which includes two orthogonal faces having a respective array of electrodes.

The physical dimensions of the DBS device can vary depending on particular configurations and desired uses. In one aspect, the device can be from about 0.1 millimeter (mm) to about 3 mm wide. In another aspect, however, the device can be sized to approximate the width of traditional DBS devices. Some traditional devices are approximately 1.27 mm wide. Many of these devices, however, have a greater cross-sectional area due to the more or less cylindrical or solid shapes throughout this 1.27 mm width. The DBS device having a plus shape, however, can be less than 10% of the cross-sectional area of such traditional devices with over 25% more cross-sectional perimeter, thus reducing the degree of neural damage as the DBS device is inserted and positioned, while increasing the surface area accessible for charge delivery. Typically, the cross-sectional shape can be formed of various intersecting planes having a width and thickness. Plane thickness can vary from about 0.01 mm to about 0.5 mm, although in most cases ranges from about 0.05 mm to about 0.2 mm. Accordingly, the cross-sectional area can be less than 20%, in some cases less than 10%, and in other cases less than 6% of a circular area having the same overall width. In addition, the present DBS device can reduce the number of insertions as the electric field is configurable to be moved off-center from the device, as described below. Each insertion of a lead (e.g., electrode) or traditional DBS device can create approximately 150 mm$^3$ of neural lesions. A traditional DBS can take up to an average of ~5 insertions for correct placement, which can destroy approximately 750 mm$^3$ of brain tissue. The present device may lesion approximately 10-30 mm$^3$ of tissue. However, with charge steering capabilities, far fewer insertions can be involved to obtain effective positioning.

Additionally, the DBS device can be made in a variety of lengths, depending on the design and usage of the device. In one aspect, the DBS device has a length sufficient to penetrate into a target neural area of a subject. In another aspect, the DBS device has a length sufficient to contain the array of electrode contacts. Furthermore, the electrode contacts can be distributed over a narrow to wide region of the device body, depending on the desired use of the device. Although electrode contacts can vary in size, typical dimensions can range from about 0.05 mm to about 0.2 mm, and in some cases 0.01 mm to about 1.0 mm. As such, a DBS device can be designed in numerous ways to allow effective stimulation and electrical current steering in the brain and in many cases such designs can be tailored to particular medical uses. In other words, it is contemplated that one level of configurability is encompassed by the pattern of activation of the electrode contacts, while another level of configurability is encompassed by the physical design of the device and/or the distribution pattern of electrode contacts.

In another aspect, distal semiconductor circuitry (312 of FIG. 9), which can also be the site for charge delivery, can be wire bonded with conductive traces such as 75 micron gold wires to a connector that sits outside the skull and can be connected to an Implantable Pulse Generator (IPG), located in the chest of the subject. The IPG can include control circuitry, power and stimulation settings, and a power supply (e.g., charging coil). The IPG can be used to control the array of electrodes of the DBS device, generate pulsatile signals for stimulation, and communicate wirelessly with an external device (e.g., ex vivo). The wireless protocol between the external device and the IPG can be a proprietary standard. Although not typically used, in an example, the wireless protocol may also use the Institute of Electrical and Electronics Engineers (IEEE) 802.15 (or Bluetooth) standard or the IEEE 802.11 (or WiFi) standard. The conductive traces can be encased in a bio-compatible epoxy to stiffen the device for insertion into brain tissue.

The following description relates to a plus shape DBS device 100 although these principles can also be applied to alternative shapes. The description of the DBS device using a plus shape is for simplicity of illustration, and it is noted that the description applies to devices having other geometrical shapes, numbers of electrodes or other variations. To show the functionality of a plus shape DBS device, the charge steering capabilities can be simulated by modeling (e.g. COMSOL 4.2, a finite element modeling program). COMSOL Multiphysics is a finite element analysis (FEA), solver and simulation software/FEA software package for various physics and engineering applications. Such computer simulations can show backwards-compatibility with traditional DBS devices, such as the state of the art DBS (e.g., sotaDBS) device. As such, as is shown in FIGS. 3A-3B, the plus shape DBS devices can generate similar electrical fields as compared to cylindrical DBS devices 102 (FIGS. 4A-4B). FIG. 3A shows a side view of a simulated electric field from a plus shape DBS electrode, and FIG. 3B shows an axial view of a simulated electric field from a plus shape DBS electrode according to aspects of the present disclosure. FIG. 4A shows a side view of a simulated electric field from a cylindrical DBS electrode (e.g., sotaDBS), and FIG. 4B shows an axial view of a simulated electric field from a cylindrical DBS electrode (e.g., sotaDBS). FIGS. 3A-6B indicate electric fields generated by a stimulation amplitude of 3V. Various shading indicates iso-voltage boundaries at 2.7 volts (V) (150, 160, 170, and 180), 2.1 V (152, 162, 172, and 182), 1.5 V (154, 164, 174, and 184), 0.9 V (156, 166, 176, and 186) and 0.3 V (158, 168, 178, and 188). The nearly identical fields may only differ within 300 microns of the present DBS device surface, where voltage contours follow the geometry of the device. As demonstrated, the plus shaped DBS device can generate nearly identical electric fields to those made by traditional sotaDBS devices. Accordingly, replacing a sotaDBS with the present DBS device may not result in a loss of functionality.

Figure 5B:
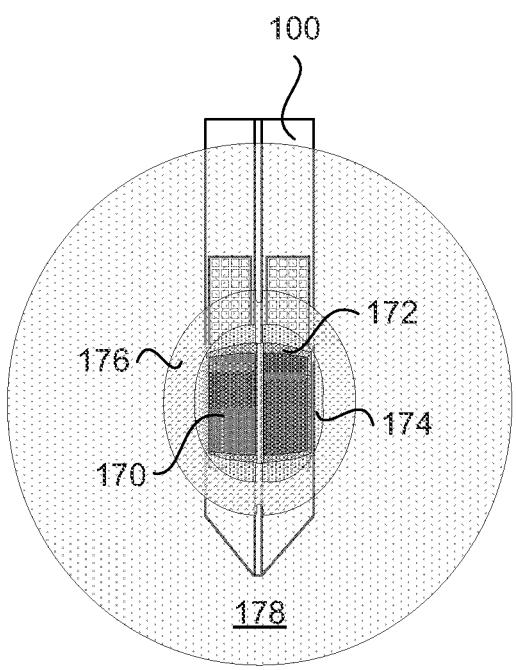
FIG. 5B illustrates an axial view graphical representation of simulation data showing isopotential surfaces (e.g., electric fields) using a deep brain stimulating device in accordance with an example.

As has been described, intricate contact geometries can be simulated to show various capabilities of electrical charge steering. FIG. 5A-5B shows a simulation whereby a generic charge spheroid can be moved off-center (i.e., the center of the charge spheroid field lies outside of the electrode boundaries). The axial view of the plus shape DBS device showing the voltage contours, illustrated in FIG. 5A, shows the capability of the plus shape DBS device to direct charge in a specified direction away from the center of the device. Voltage contours can be rotated axially around the device with precision by controlling the device settings to allow customizability of the charge field for an individual patient.

Figure 6A:
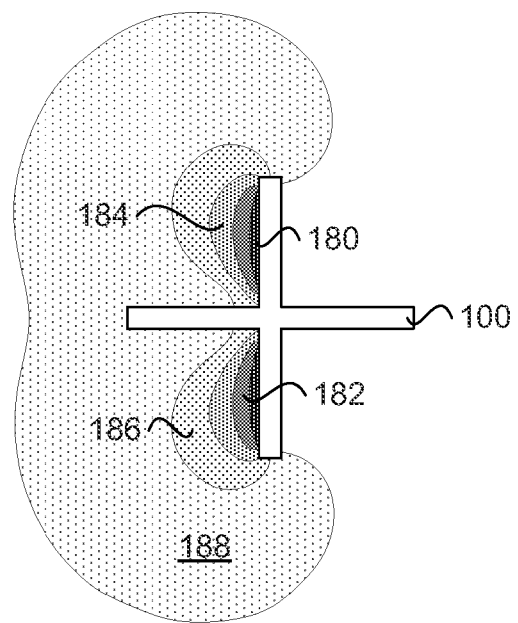
FIG. 6A illustrates a side view graphical representation of simulation data showing a heart-shaped electric field using a deep brain stimulating device in accordance with an example.
Figure 6B:
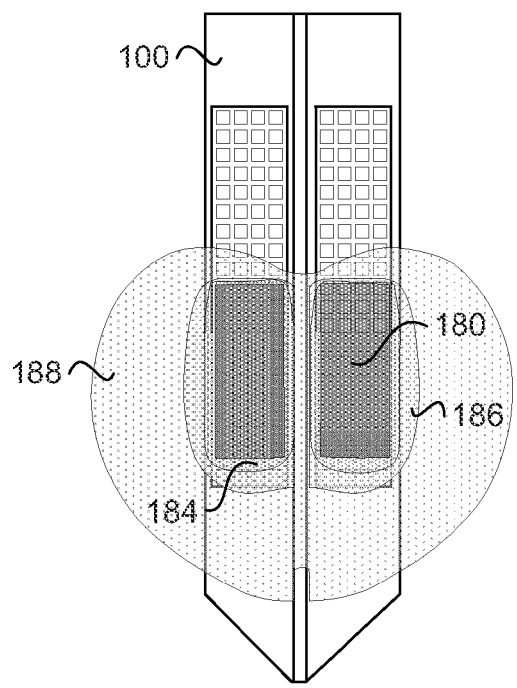
FIG. 6B illustrates an axial view graphical representation of simulation data showing a heart-shaped electric field using a deep brain stimulating device in accordance with an example.

Additionally, the present DBS device can produce numerous unique electrical charge distributions. For example, electrical charge can be driven precisely in one direction away from the electrode, using the geometry of the electrode itself to steer the charge and prevent leakage into neighboring areas, as shown in FIGS. 6A-6B. FIG. 6B illustrates a side view of a shape of iso-potential shells with a complex geometry (e.g., a heart shape). FIG. 6A illustrates an axial view of the complex geometry of FIG. 6B. In addition, by selecting the appropriate electrode contacts, various non-spheroidal shapes of electrical charge distribution can be produced. The capabilities of such a device can provide treatment benefits which are enabled by a high level of control over the placement of electrical charge. Such controllability allows for significant customization of the electrical field over a given tissue volume while considering unique patient anatomy of target structures that the device will be used to stimulate. For example, deep brain structures are rarely if ever spherical, and the configurable electrode allows a fitting of electrical charge distribution to the anatomy and response profile of the subject. Indeed, even if the anatomy did consist of spheres, it is unlikely that the electrode can be placed in the exact center of such a sphere (e.g., errors in placement). Traditional DBS devices, such as the sotaDBS, may not be able to effectively control the electrical charge distribution. Accordingly, when such traditional DBS devices are placed off-center, stimulation settings may be reduced so that electrical charge does not leak outside of the neural area to be stimulated in order to prevent side effects, which can result in a less effective treatment with the traditional DBS devices.

The circuitry design utilized to provide functionality to a DBS device can be highly varied depending on numerous design paradigms. In one aspect, the circuitry can be designed and configured to couple to and be functionally integrated with traditional stimulator devices and medical insertion and delivery protocols. In other aspects, the device and or circuitry can be designed to correspond to future stimulator devices. In one specific aspect, however, the circuit design for a DBS stimulator can use a cascade of flip flops (e.g., shift register), thus allowing up to many thousands or more electrical contacts without the need for a large quantity of physical wires. A flip-flop or latch (e.g., delay or data flip-flop (D flip-flop)) is a circuit that can have two stable states (e.g., one or zero; active or inactive) and can be used to store state information. A flip-flop can be a bistable multivibrator.

In an example, a shift register can limit the number of wires running from the DBS device (e.g., in the brain) to the IPG (e.g., in the chest) to a minimum. Other circuitry may also be used to reduce the number of wires used in the extension which can achieve a similar effect. In another example, other circuitry and more extension wires may be introduced into the design.

A continuous shift register for the entire device can be used to serially control the DBS device. For example, an array of electrodes on a face of a substrate can have 8 contacts wide by 55 contacts deep for a total of 440 positions. Storing 2 bits at each position (e.g., 4 states), the 440 positions can have 880 latches, yielding $4^{440}$ possible configurations. Since each chip or face of the substrate can have its own bond pads, the chips can either be daisy-chained together to make one continuous device, or each chip can be wire-bond to a dedicated signal/clock line, which can create four independent registers. Daisy-chaining the chips together can reduce the number of wire and registers, but may be prone to greater failure due to a longer register. An advantage to separating and addressing each chip individually can be a 75% reduction in programming time, but a disadvantage can be using more wires. In addition, addressing each chip individually can provide isolation between chips if one chip goes bad, the other three chips can still be useful.

With a shift register, the contact states may not be addressed in parallel. Although, recording and stimulating with the DBS device may occur in parallel. When recording with the DBS device, many contacts can be set to a same channel (e.g., parallel to serial) for recording on that line.

FIG. 7 illustrates digital logic to control a contact transmission gate 236 and 238 for a single electrode 224 using two latches 230. The two bits of information from the latches can switch the electrode from an anode 210, cathode 212, or common 214, where the common is a voltage between the anode and cathode voltages. In an example, a common connection can be a ground voltage. Each electrode can be controlled by a single input 220 and a clock 222. The shift register can store a bit of information at each position in the register. When a clock signal 222 is presented to the register, the bit can move to the next position. The cycle of the clock and the bit movement can be repeated many times so that each position in the register can be assigned its own bit, where each bit (or each two bits) can represent control signaling for an electrode in the array of electrodes of the DBS device. The digital logic can also include AND gates 232 and inverters 234. It can be beneficial for a DBS device to have each electrical contact/electrode function as an anode, a cathode, floating, or a common. In such cases, the anode and cathode are used for stimulation purposes. Floating refers to an electrode having no electrical connection to any circuitry. Common is similar to floating, only with all common contacts connected together. Common mode may be useful for recording purposes, for example, to aide in the surgical placement of the device. Since each position in the shift register can store one bit of information, and two bits can be useful to control the four possible connections at each contact, two register positions can be used for each electrical contact. To get four control signals from two bits of information, digital logic can be utilized. In essence, both bits can be split and each passed through an inverter 234, thus yielding four lines. Combinations of the first and second bit can be passed through AND gates 232 in a way that only one AND gate is ever active at a time. The active AND gate activates a switch that connects the electrode contact to the specified line: Anode, cathode, or common. FIG. 7 shows a circuit schematic for a single electrode contact. In this schematic, two flip flops 230 read in the two bits of information from an input (one input is delayed). The information from the flip-flops is transmitted to the AND gates as a combination of first and second bits, with some lines being inverted. The AND gates output is inverted so that it may control a transmission gate which can require both high and low signals to be ON.

The circuit illustrated in FIG. 7, which can be sufficient for controlling one contact, can be repeated in an array, one for each metal contact as is shown in FIG. 8. FIG. 8 illustrates a generalized layout of a digital circuit for a single electrode in the array of electrodes. The generalized layout can include an electrode contact area 250 controlled by switches 260A-C to bus lines 252A-C for the anode, common and cathode, respectively (252C bus not shown). The circuitry can include a shift register 262, and digital logic 264 (e.g., inverters and AND gates). By chaining together the information from one electrode contact circuit to the next, only one signal and a clock line can control all contacts, passing contact state down the register. In this way, the number of wires from the DBS can be reduced. For example, a need for thousands of wires coming from the DBS device to the wire bond contacts can be eliminated.

Figure 9:
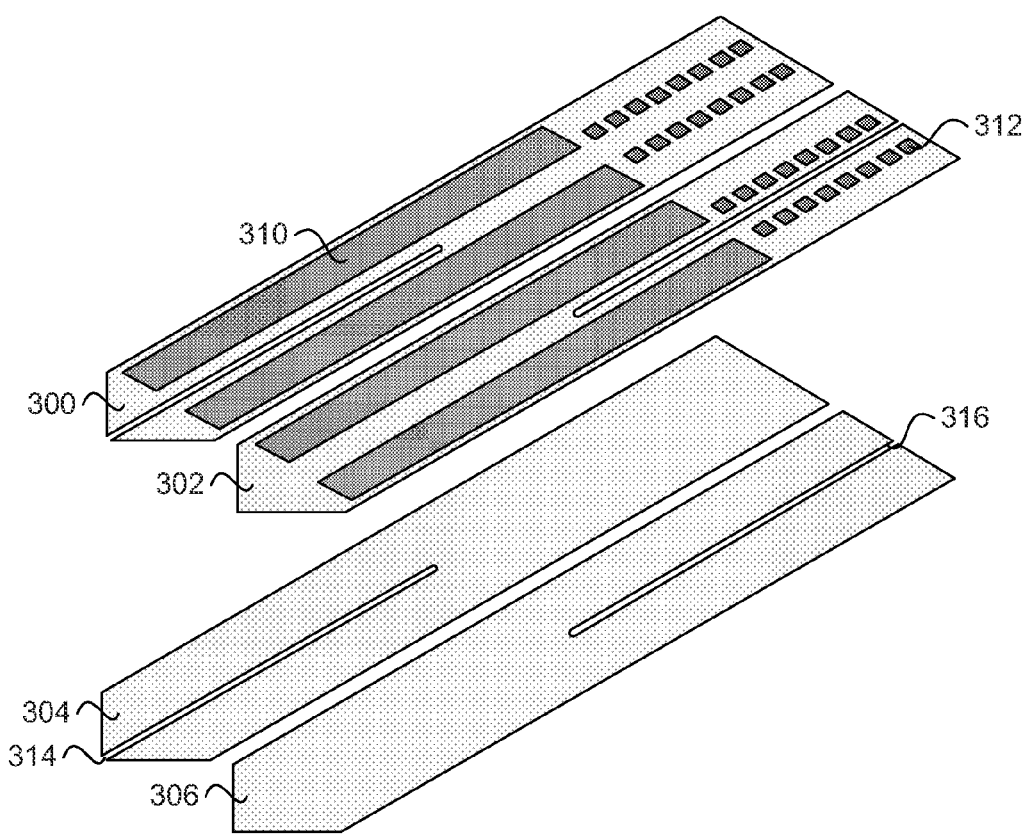
FIG. 9 illustrates a graphical representation of silicon chip pieces during assembly of a deep brain stimulating device in accordance with an example.

Post-fabrication modifications can be made to the silicon chips following complementary metal-oxide-semiconductor (CMOS) processing. For example, it may be useful to trim the wafer to a desired shape for making the DBS device, as illustrated in FIG. 9. The desired shape can be created using Deep Reactive Ion Etching (DRIE) or any other suitable technique which can include, but is not limited to CNC machining, etching, and the like. In other words, structural changes can be made to facilitate insertion and delivery of the device into neural tissue. For example, an assembly groove 314 and 316 can be inserted and the ends of the wafers can be formed to a point. Anode and cathode bus lines, which deliver stimulation power to each contact in the circuit, can be fabricated on top of the circuit components. Thus, a several-micron-thick metal layer can be laid down on the entire wafer piece, and then portions selectively removed by lift-off. An insulating layer can also be applied over the entire chip. It can also be useful to etch vias to the electrode contacts 312 and then plate metal thereon. The metal can be etched to reveal electrode contacts of a biocompatible material such as, for example, platinum, gold, or sputtered iridium-oxide. After finishing circuit modifications it can also be useful to thin the wafer to its final thickness. Thinning can be accomplished using any known technique, such as for example, using a dicing saw that will make multiple passes across the back and chemical etching of the wafer itself (e.g. by chemical mechanical polishing (CMP)).

Each semiconductor substrate 300, 302, 304, and 306 can include electrode array surface, circuitry to control the electrode array 310, and contacts 312 for wire bonds used to connect the DBS device 100 to an external device (e.g., implanted pulse generator external to the DBS device) via an extension.

Figure 10A:
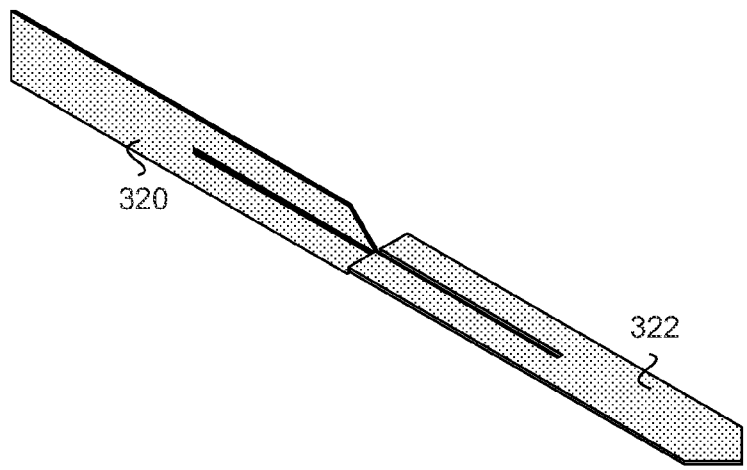
FIGS. 10A-C illustrate a graphical representation of silicon chip pieces formed into a plus shape during assembly of a deep brain stimulating device in accordance with an example.
Figure 10B:
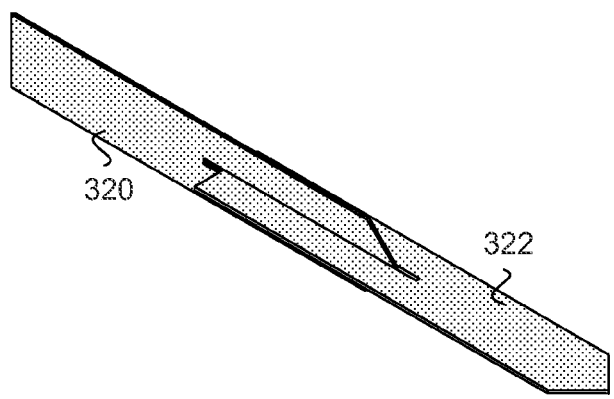
Figure 10C:
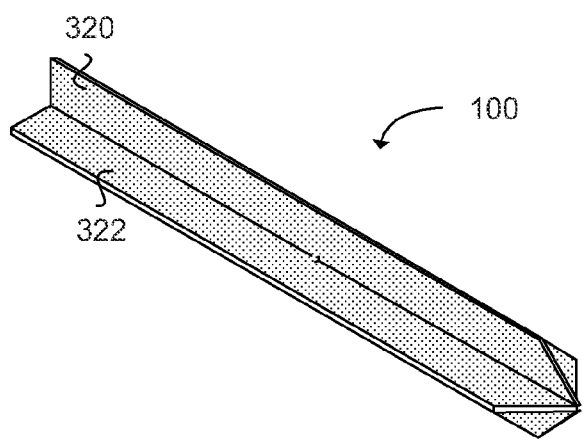

In one aspect, a DBS device 100 can be constructed having a plus shape by attaching multiple silicon chip assemblies together to form each electrode array surface. For example, 50 micron (μm) thick wafers sections 300-306 can be placed back-to-back 300 with 304 and 302 with 306 (i.e., the array of electrodes 310 facing outward) with glue and allowed to cure, as shown in FIG. 9. In the initial gluing, pairs (300 with 304 and 302 with 306) of silicon chips can be bonded together back-to-back. Non-limiting examples of suitable glue can include silicone, polyamide and biocompatible acrylic or epoxy. Matching assembly grooves 314 and 316 can be aligned, glued, and allowed to bond, with care taken to keep glue from the groove. The glued pieces 320 and 322 can then be aligned and assembled by aligning the assembly grooves, as is shown in FIGS. 10A-10C. In this case, assembly can start with two halves that were previously glued (FIG. 9) being slid together at the assembly grooves (FIGS. 10A-10B). Once inserted fully into position (FIG. 10C), the glue between the two halves can be remelted with pressure applied to external faces of the device. This pressure can squeeze a small amount of glue from between the thinned chips that can then adhere to the perpendicular face of the opposite chip pieces. The glue can be allowed to cure, thus binding the pieces together along the center line. As an alternative, glue can be applied to the two halves for attachment, either prior to or following assembly.

In another example, the DBS device 100 can be assembled without melting glue. Stiff epoxy can encase the wire bonds (e.g., attached to the contact 312) at the upper end of the '+' in the DBS device. The pointy end (e.g., the other end) can be lightly dipped into a very thin glue (e.g., biocompatible cyanoacrylate), which can flow up the cracks and between the chips for a couple mm due to capillary action. The small amount of glue can be sufficient to hold the two substrate planes together in the plus shape.

Further packaging can be performed on the assembled silicon chip device. For example, wire bonding among the various silicon chip elements can be performed to enable electrical interconnectivity. Electrical interconnectivity can be useful for the sharing of the one serial line and the one signal line, but can also have the benefit of eliminating or reducing a four-time repetition of wires common to all chips. In one aspect, one of the silicon chips can have wire connections that lead to the connector located outside the skull of the subject. For example, the wire connections can include seven 75 μm gold insulated wire bonds. By varying the length of the wire connections, the DBS device length can be altered to target brain regions at different depths. The wire connections can be encased in a biocompatible epoxy that can lend the whole assembly a greater stiffness to further support the device during implantation.

Sample Implementation

In an example, to assess the robustness of a silicon plus-shaped DBS device during handling and assembly, blank silicon wafers that had been thinned to about 100 μm were etched to the shape of one DBS device plane, enabling mechanical testing of the silicon substrate. As a first test, the setup of Deep Reactive Ion Etching (DRIE) equipment for etching wafer pieces was evaluated. The high-aspect-ratio DRIE process can cut nearly-vertical trenches in silicon wafers. To accomplish this, a wafer with exposed, thick, SU-8 , photoresist was placed in the DRIE chamber. The chamber was evacuated to low pressure. A plasma was lit inside the chamber that selectively etches silicon and not the photoresist. To overcome isotropic etching, the plasma was cycled with a passivation stage every few seconds. Thus, each newly etched trench was completely passivated, and when the next round of plasma began, the plasma etched the bottom of the trench first, leaving the sidewalls intact. Throughout this process, inert helium flowed along the back of the wafer to prevent heating from plasma striking the surface. The helium and all other components were kept cool by liquid nitrogen.

For etching the DBS wafer pieces, a blank, 100 µm thin silicon wafer was mounted onto a substrate wafer with wafer wax. This substrate is convenient for handling as the substrate gives a user something more substantial to hold, and useful for DRIE so that when individual pieces have been etched from the thin wafer, the pieces can be held in place to the substrate and not lost in the helium flow. The substrate was placed on a hot plate, and solid wax, which is soluble in acetone, was melted directly onto the surface. The solid wax was applied directly to a hot wafer which caused melting of the wax. While still liquid, a thinner wafer was placed on top and air bubbles were removed. The stacked assembly (i.e., a thick wafer on the bottom, an intermediate wax adhesion layer, and a thin wafer on top) was then removed from the hot plate and allowed to cool. When processing was complete, acetone was used to remove the wax, which released the thinned wafer pieces from the thicker substrate holder.

After testing the DRIE setup and having several good runs through the process, some silicon wafer pieces were assembled into a plus-shaped device. Pieces having distal and proximal center cuts were fitted together by hand. No special tools or jigs may be needed to slide the pieces together. However, pieces that are not cleaned of photoresist can sometimes stick and then break. It was thus useful to make sure the pieces were cleaned well of photoresist prior to assembly. Also, this test differs from final assembly in another matter. For a net thickness of 100 µm, a pair of 50 µm thick CMOS silicon pieces can be joined back-to-back to have circuitry present on both sides. Joining silicon pieces together can be completed before assembly, however, as joining can provide an advantage. When gluing pieces back-to-back, a slight excess of glue can be applied to the pieces. After assembly, the glue can be remelted with slight pressure placed on both faces of the device. The process can squeeze excess glue onto the perpendicular wafer, securing the '+' shape. Although glue was used to join the silicon pieces together in this example, other examples can form the plus shape without excess glue between the pieces, as previously described.

To test the ability of the wafer to be placed into brain tissue, a mechanical stimulant of brain tissue was used. An agar gel, mixed at 0.6% agar to water has roughly the same mechanical properties as brain tissue. The '+' shaped silicon pieces made in this mechanical testing phase easily penetrated the gel and showed no signs of breakage after being inserted and removed many times. Indeed, the assembled '+' shape of the device can be remarkably more robust mechanically then the individual pieces themselves due to the geometrical arrangement.

Figure 11:
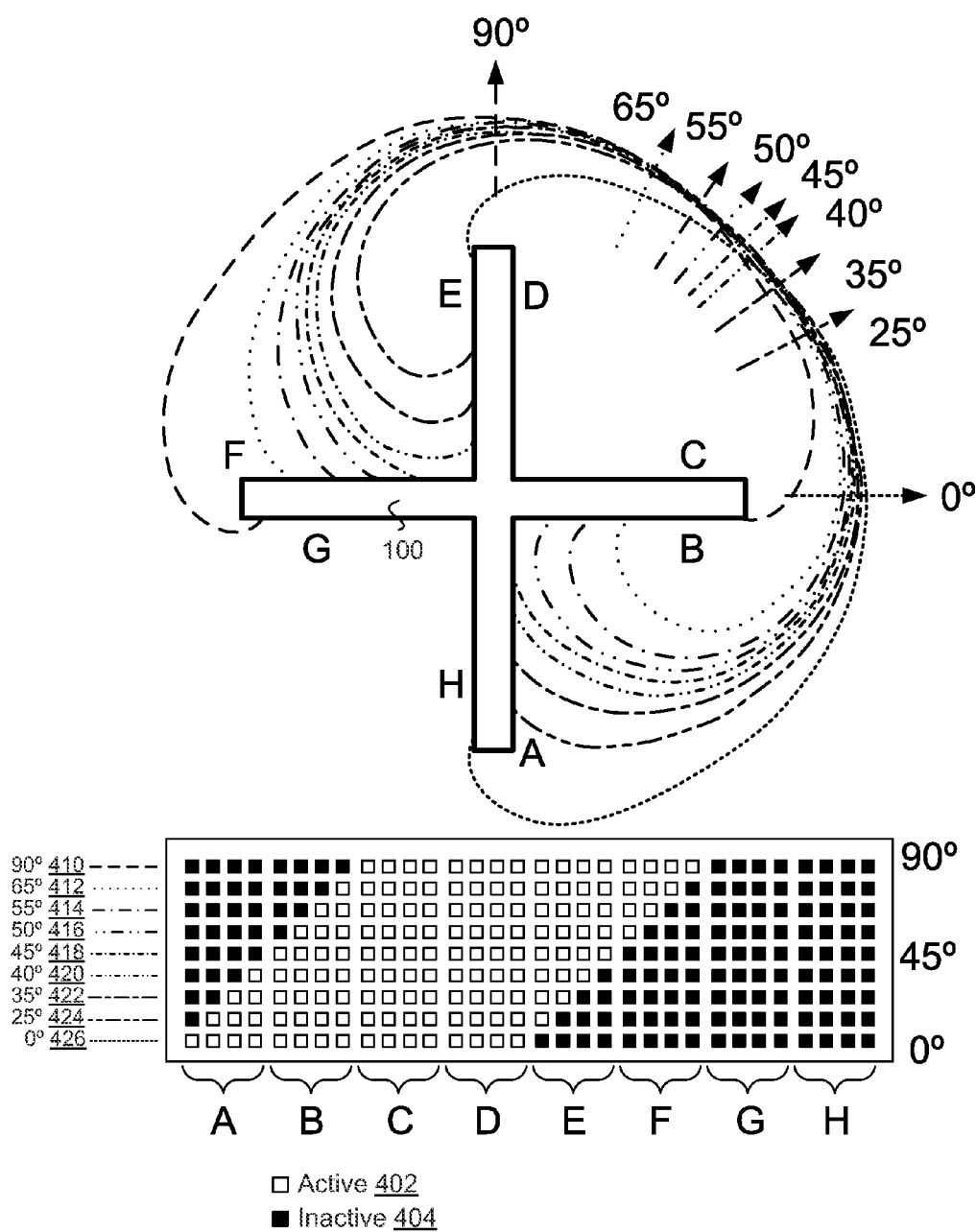
FIG. 11 illustrates a graphical representation of directing charge of a deep brain stimulating device in accordance with an example.

FIG. 11 illustrates an example of directing charge or charge steering using the DBS device 100. FIG. 11 illustrates a single row of electrodes of a plus shaped array of electrodes with 8 faces (A-H), where each face has 4 electrodes. The eight faces are unfolded into a single line of 32 electrodes (e.g., 8 faces times 4 electrodes per face) at one axial (radial) depth of the electrodes. Each electrode can be active 402 (e.g., acting as an anode or cathode) or be inactive 404 (e.g., a float or common). Based on the configuration of the 32 electrodes, the charge can be steered at various angles relative to the quadrant. FIG. 11 illustrates 9 different directions of isopotential shells (i.e., at 1.0 V) for a first quadrant of the DBS device. The directions can range from 90° (410) to 0° (426). Other directions can include 65° (412), 55° (414), 50° (416), 45° (418), 40° (420), 35° (422), and 25° (424). The nine illustrated examples of FIG. 11 show pushing a sphere-like electric field off-axis of the electrode at angles between 0° (426) and 90° (410). With other variation of the active and inactive electrode patterns other directions or angles of the isopotential shells may also be available. With a corresponding change in the electrode pattern, different directions of isopotential shells can be generated for the other three quadrants of the of the DBS device, in a similar manner to the first quadrant, as illustrated, radially covering 0° to 360° of the DBS device. While FIG. 11 illustrates different directions of isopotential shells in the axial axis, similar patterns and principles can be used to generate various charge steering isopotential shells in the longitudinal axis.

Figure 12:
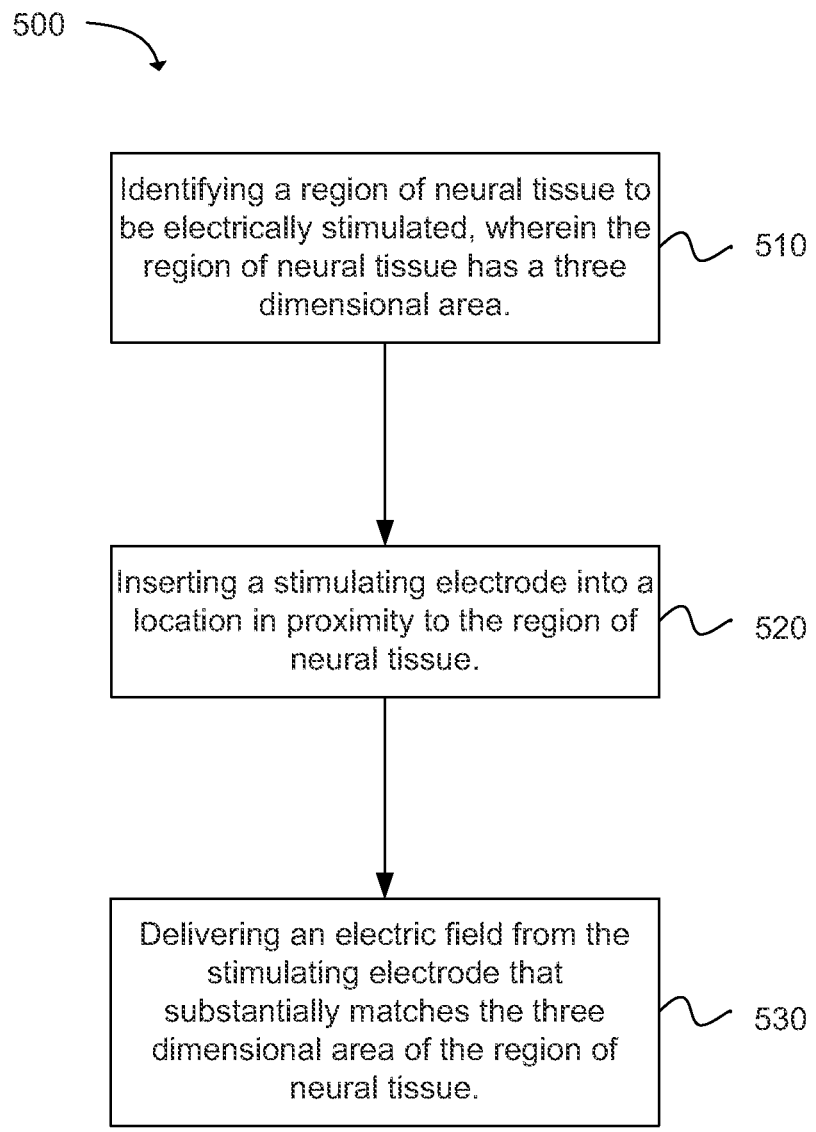
FIG. 12 depicts a flow chart of a method of stimulating a neural region in vivo in accordance with an example.

Another example provides a method 500 of stimulating a neural region in vivo, as shown in the flow chart in FIG. 12. In an example, at least a portion of the method may be executed as instructions on a machine, computer circuitry, or a processor, where the instructions are included on at least one computer readable medium or one non-transitory machine readable storage medium. The method includes the operation of identifying a region of neural tissue to be electrically stimulated, wherein the region of neural tissue has a three dimensional area, as in block 510. In one example, an anatomical MRI can be used to register the DBS electrode to the patient-specific anatomy. The patient anatomy can then be isomorphically fit to a generic brain model from a standard atlas. Known targets of optimal stimulation from the standard atlas can then be isomorphically mapped back onto the patient-specific brain. An automated computer algorithm can then be used to identify the DBS contact pattern of anodes and cathodes that will provide desired stimulation of the desired anatomical target. The operation of inserting a stimulating electrode into a location in proximity to the region of neural tissue follows, as in block 520. In another example, a DBS electrode can be intentionally implanted to the boundary of an anatomical target. An MRI can be used to register the DBS electrode to the patient-specific anatomy. The patient anatomy can then be isomorphically fit to a generic brain model from a standard atlas. The target structure from the standard atlas can then be isomorphically mapped back onto the patient-specific brain. An automated computer algorithm can then be used to identify the DBS contact pattern of anodes and cathodes that will provide optimal stimulation only in the direction of the desired anatomical target. The next operation of the method can be delivering an electric field from the stimulating electrode that substantially matches the three dimensional area of the region of neural tissue, as in block 530.

Figure 13:
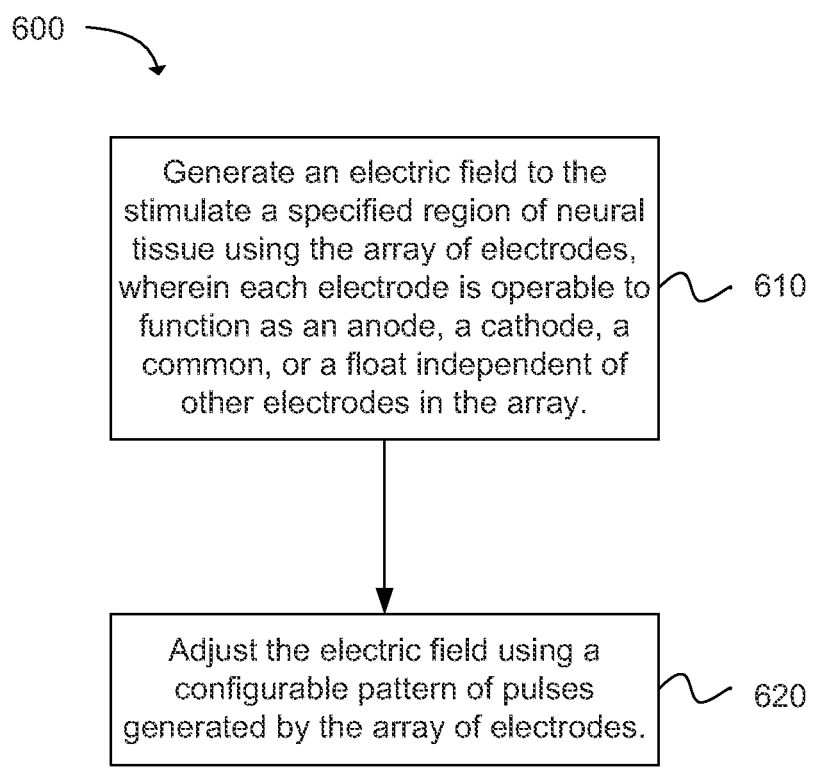
FIG. 13 depicts functionality of computer circuitry of an array of electrodes for deep brain stimulation (DBS) in accordance with an example.

Another example provides functionality 600 of computer circuitry of an array of electrodes for deep brain stimulation (DBS), as shown in the flow chart in FIG. 13. The functionality may be implemented as a method or the functionality may be executed as instructions on a machine, where the instructions are included on at least one computer readable medium or one non-transitory machine readable storage medium. The computer circuitry can be configured to generate an electric field to stimulate a specified region of neural tissue using the array of electrodes, wherein each electrode is operable to function as an anode, a cathode, a common, or a float independent of other electrodes in the array, as in block 610. The computer circuitry can be further configured to adjust the electric field using a configurable pattern of pulses generated by the array of electrodes, as in block 620.

Various techniques, or certain aspects or portions thereof, may take the form of program code (i.e., instructions) embodied in tangible media, such as floppy diskettes, compact disc-read-only memory (CD-ROMs), hard drives, non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a random-access memory (RAM), erasable programmable read only memory (EPROM), flash drive, optical drive, magnetic hard drive, solid state drive, or other medium for storing electronic data. The switch may also include a transceiver module (i.e., transceiver), a counter module (i.e., counter), a processing module (i.e., processor), and/or a clock module (i.e., clock) or timer module (i.e., timer). One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom very-large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" or "exemplary" means that a particular feature, structure, or characteristic described in connection with the example is included in at least one embodiment of the present invention. Thus, appearances of the phrases "in an example" or the word "exemplary" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A deep brain stimulating device, comprising:
  a semiconductor substrate;
  an array of electrodes coupled to the semiconductor substrate, wherein each electrode is operable to function as at least one of an anode, a cathode, a float, and a common independent of other electrodes in the array, wherein the common is a specified voltage between the anode and the cathode; and
  circuitry operable to control the array of electrodes, wherein the electrodes of the array are spatially arranged such that the circuitry is operable to selectively activate each electrode with a specified voltage to produce a unique electrical charge distribution across multiple electrodes that is steered to a targeted brain region, wherein the steered electrical charge distribution is voltage-based, the circuitry comprising a shift register associated with each electrode and operable to control each electrode, wherein an electric field is operable to be delivered in an asymmetrical pattern relative to a longitudinal axis or lateral axis of the deep brain stimulating device.

2. The device of claim 1, wherein each electrode is further operable to selectively function as the cathode, the float, and the common, wherein each electrode further includes a digital circuit comprising an anode switch, cathode switch, common switch each operable to selectively function the associated electrode as at least one of the cathode, the float, and the common.

3. The device of claim 2, wherein the digital circuit of each electrode comprises a single input and a clock, wherein each electrode is controlled by the single input and the clock.

4. The device of claim 3, wherein the circuitry comprises a signal line and a clock line, wherein the signal line is coupled to the single input of each electrode and wherein the clock line is coupled to the clock of each electrode, such that the signal line and the clock line controls all electrodes, thereby passing contact state down the shift register.

5. The device of claim 3, wherein the digital circuit of each electrode comprises a pair of latches operable to switch the associated electrode as at least one of the cathode, the float, and the common.

6. The device of claim 5, wherein each switch comprises an AND gate, an inverter, and a transmission gate, wherein signals from the pair of latches are passed through the AND gate of each switch, and inverted by the associated inverter to control the associated transmission gate, such that only one AND gate is active at a given time to activate the selected at least one of the anode switch, cathode switch, and common switch.

7. The device of claim 1, wherein the semiconductor substrate includes at least two surfaces and each surface includes at least two columns of electrodes and at least two rows of electrodes.

8. The device of claim 1, wherein the array of electrodes includes from about 50 to about 25,000 electrodes.

9. The device of claim 1, wherein the array of electrodes includes from about 5000 to about 15,000 electrodes.

10. The device of claim 1, wherein the array of electrodes includes greater than 25,000 electrodes.

11. The device of claim 1, wherein the semiconductor substrate includes at least two surfaces that are perpendicular to one another, wherein each of the two surfaces includes a portion of the array of electrodes.

12. The device of claim 11, wherein the semiconductor substrate is formed into a plus shape having eight perpendicularly opposed surfaces, wherein each of the eight perpendicularly opposed surfaces includes a portion of the array of electrodes.

13. The device of claim 1, wherein the semiconductor substrate includes the circuitry operable to control the array of electrodes, wherein the shift register comprises a continuous shift register operable to serially control the array of electrodes.

14. A deep brain stimulating system using the deep brain stimulating device of claim 1, comprising:
the deep brain stimulating device of claim 1;
an implanted pulse generator; and
an electrical connection extension electrically coupling the circuitry of the deep brain stimulating device to the implanted pulse generator.

15. The device of claim 1, wherein the semiconductor substrate includes four wafer sections formed into a plus shape, wherein the four wafer sections are comprised of a pair of vertical wafers planarly coupled together and defining a front groove, and a pair of horizontal wafers planarly coupled together and defining a rear groove, wherein the pair of vertical wafers and the pair of horizontal wafers are coupled to each other via the front and rear grooves to form the plus shape.

16. The device of claim 1, wherein the circuitry comprises a signal line and a clock line, wherein the signal line is coupled to a single input of each electrode and wherein the clock line is coupled to a clock of each electrode, such that the signal line and the clock line controls all electrodes, thereby passing contact state down the shift register.

17. The device of claim 1, wherein the shift register comprises a bistable multivibrator.

18. The device of claim 1, wherein the shift register comprises a continuous shift register operable to serially control the array of electrodes.

19. A method of stimulating a neural region in vivo, comprising identifying a region of neural tissue to be electrically stimulated, wherein the region of neural tissue has a three dimensional area;
inserting the deep brain stimulating device of claim 1 into a location in proximity to the region of neural tissue; and
delivering an electric field from the deep brain stimulating device that substantially matches the three dimensional area of the region of neural tissue.

20. The method of claim 19, wherein the location in proximity to the region of neural tissue is in a portion of the three dimensional area.

21. The method of claim 19, wherein the electric field is delivered in an asymmetrical pattern relative to a longitudinal axis or lateral axis of the deep brain stimulating device.

22. The method of claim 19, wherein delivering the electric field from the deep brain stimulating device that substantially matches the three dimensional area of the region of neural tissue further comprises:
delivering the electric field from the deep brain stimulating device that estimates the three dimensional area of the region of neural tissue;
measuring the electric field from the deep brain stimulating device relative to the region of neural tissue; and
adjusting the electric field of the deep brain stimulating device to substantially match the three dimensional area of the region of neural tissue.

23. The method of claim 19, wherein delivering the electric field from the deep brain stimulating device that substantially matches the three dimensional area of the region of neural tissue further comprises:
delivering the electric field from the deep brain stimulating device that estimates the three dimensional area of the region of neural tissue;
evaluating the effect of the electric field from the deep brain stimulating device; and
adjusting the electric field of the deep brain stimulating device based on the effect to minimize adverse side effects of the electric field.

24. The method of claim 19, futher comprising controlling each electode with a single input and a clock of a digital circuit of the associated electrode, and selecting each electrode to function as at least one of the cathode, the float, and the common, wherein the digital circuit of each electrode includes an anode switch, cathode switch, common switch.

25. A deep brain stimulating device, comprising:
a semiconductor substrate;
an array of electrodes coupled to the semiconductor substrate, wherein each electrode includes a digital circuit comprising an anode switch, cathode switch, common switch each operable to selectively function the associated electrode as at least one of the cathode, the float, and the common, and wherein the digital circuit further comprises a single input and a clock, such that each electrode is controlled by the single input and the clock; and circuitry operable to control the array of electrodes and comprising a signal line and a clock line, wherein the signal line is coupled to the single input of each electrode and wherein the clock line is coupled to the clock of each electrode, such that the signal line and the clock line controls all electrodes, thereby passing contact state down a shift register, wherein the electrodes of the array are spatially arranged such that the circuitry is operable to selectively activate each electrode with a specified voltage to produce a unique electrical charge distribution across multiple electrodes that is steered to a targeted brain region, wherein the steered electrical charge distribution is voltage-based.

26. The device of claim 25, wherein the digital circuit of each electrode comprises a pair of latches operable to switch the associated electrode as at least one of the cathode, the float, and the common.

27. The device of claim 25, wherein the semiconductor substrate includes four wafer sections formed into a plus shape, wherein the four wafer sections are comprised of a pair of vertical wafers planarly coupled together and defining a front groove, and a pair of horizontal wafers planarly coupled together and defining a rear groove, wherein the pair of vertical wafers and the pair of horizontal wafers are coupled to each other via the front and rear grooves to form the plus shape.

* * * * *